(12) United States Patent
Kessler et al.

(10) Patent No.: US 6,403,506 B1
(45) Date of Patent: Jun. 11, 2002

(54) GLASS POWDER AND USE THEREOF

(75) Inventors: Susanne Kessler; Hartmut Paschke, both of Ergolding; Hans-Werner Beudt, Wiesbaden; Susanne Kiermayer, Rottenburg/Niedereulenbach, all of (DE)

(73) Assignee: Schott Glas, Mainz (DE)

( * ) Notice: Subject to any disclaimer, the term of this patent is extended or adjusted under 35 U.S.C. 154(b) by 0 days.

(21) Appl. No.: 09/629,090

(22) Filed: Jul. 31, 2000

(30) Foreign Application Priority Data

Jul. 29, 1999 (DE) .......................... 199 35 707

(51) Int. Cl.⁷ .............................. C03C 21/00
(52) U.S. Cl. ........................ 501/11; 501/14; 501/15; 501/16; 501/17; 501/18; 501/19; 501/20; 501/21; 501/22; 501/23; 501/24; 501/25; 501/26; 106/35
(58) Field of Search .............................. 106/35; 201/11, 201/14, 15, 16, 17, 18, 19, 20, 21, 22, 23, 24, 25, 26

(56) References Cited

U.S. PATENT DOCUMENTS

| | | | | |
|---|---|---|---|---|
| 3,370,966 A | * | 2/1968 | Schwartz et al. | 501/15 |
| 3,649,311 A | * | 3/1972 | Araujo | 501/66 |
| 3,964,919 A | * | 5/1976 | Ray et al. | 504/45 |
| 4,099,977 A | * | 7/1978 | Francel et al. | 501/15 |
| 4,358,549 A | | 11/1982 | Randklev et al. | 523/117 |
| 4,591,384 A | * | 5/1986 | Akahane et al. | 106/35 |
| 5,466,285 A | * | 11/1995 | Kamiya et al. | 106/35 |
| 6,087,282 A | * | 7/2000 | Panzera et al. | 106/35 |
| 6,187,701 B1 | * | 2/2001 | Sekino et al. | 106/35 |

FOREIGN PATENT DOCUMENTS

GB  2323366  9/1998

* cited by examiner

*Primary Examiner*—C. Melissa Koslow
(74) *Attorney, Agent, or Firm*—Millen, White, Zelano & Branigan, P.C.

(57) ABSTRACT

The invention relates to a glass powder, where at least one oxidizing agent or one reducing agent is added to the glass powder. The glass powder is preferably used as dental glass powder.

15 Claims, No Drawings

GLASS POWDER AND USE THEREOF

The invention relates to a glass powder and use thereof.

BACKGROUND OF THE INVENTION

Glasses and glass powders produced therefrom often contain polyvalent cations, be they in the form of a component added deliberately to the glass mixture, for example for coloring a glass or for setting a certain glass property, or be they in the form of impurities or contaminants, which are sometimes present only in traces, in the respective mixture components or in the containers in contact with the mixture or the melt.

The oxidation number of the polyvalent cations is essentially set by the process procedure during the glass melting (reducing or oxidizing melting), by the mixture or glass composition and/or by the type and amount of fining agent used. Undesired flecks of color can, for example, be removed during fining by using suitable fining agents.

Because of external influences, for example during the further processing or post-treatment of a glass or a glass powder, the oxidation number of the polyvalent cations can change unfavorably.

Particularly in the case of glasses or glass powders in which retention of a certain oxidation number is essential even after further processing, e.g. the retention of a certain coloration or a certain glass property, the change in oxidation number caused, for example, by external oxidative or reductive influences is troublesome, or the glasses or glass powders changed in this way are entirely useless for further use.

On the other hand, a deliberate, subsequent change in the oxidation number, set during the melting, of a polyvalent glass component may be desired and appropriate.

The retention of a certain coloration is frequently absolutely necessary, particularly in the case of glass powders for use in the dental sector, for example in a dental glass/plastic composite for tooth filling. Color changes resulting from a further processing procedure or a post-treatment of the dental glass powder would render the glass powder useless. Traces of impurities in the glass components are often sufficient to cause undesired color changes during the further processing of a dental glass powder.

SUMMARY OF THE INVENTION

The object of the invention is therefore to provide a glass powder in which the oxidation number of at least one glass component does not change or changes only slightly, in particular in the case of further processing or post-treatment of the glass powder, for example as a result of external oxidative or reductive influences. It is also an object of the invention to provide a glass powder in which the oxidation number of at least one glass component can be subsequently set in a targeted manner. The glass powder is preferably particularly suitable for us in the dental sector, but any glass powder which will undergo melting can be used. Suitable glasses are disclosed in, e.g., DE 199 49 385 Al; DE 44 43 173 Al; U.S. Pat. No. 5,641,347 and DE 43 23 143 C1.

To achieve this object, a glass powder is provided according to the invention, where at least one oxidizing agent or one reducing agent is added to the glass powder.

By adding at least one oxidizing agent or one reducing agent to the glass powder in accordance with the invention, a change in the oxidation number of a glass component, in particular while external oxidative or reductive influences act on the glass powder, is avoided in an advantageous and simple manner.

If the glass powder is subjected to an oxidative influence, a reducing agent is added to the glass powder. If reductive influences take effect, for example during a post-treatment, an oxidizing agent is added to the glass powder. The type and amount of oxidizing agent or reducing agent are chosen such that the external influence in each case is just counteracted. Preferably, 0.01 to 1% by weight, in particular 0.5% by weight, of oxidizing agent or reducing agent is added to the glass powder.

The change in the oxidation number of a glass component caused by external influences is prevented as a result or kept so low that the proceeding redox reaction is counteracted by providing an appropriate redox partner.

The oxidation number of at least one glass component can, however, also advantageously be subsequently set in a targeted manner. If the oxidation number is to be increased, at least one oxidizing agent is added to the glass powder. If, on the other hand, a reduction in the oxidation number is desired, then a reducing agent is added to the glass powder. In this connection as well, the type and amount of oxidizing agent or reducing agent can be easily determined experimentally.

The amount and type of oxidizing agent or reducing agent added further depend, in particular, on the glass powder composition, the particle size distribution and the specific surface area, and on the respective external influences, for example during further processing (e.g. temperature; time; pressure; oxidative or reductive atmosphere).

The oxidizing agents or reducing agents can be added to the glass powder in solid, liquid or gaseous form.

If, during a thermal post-treatment of a glass powder, a reduction of at least one glass component takes place, or if the oxidation number of at least one glass component is to be increased in a targeted manner, then the oxidizing agent $NH_4ClO_4$ is preferably added to the glass powder. Particular preference is given to adding 0.5% by weight of $NH_4ClO_4$ to the glass powder. Virtually all conventional oxidizing or reducing agents can be used in the invention. Such agents are commercially available or obtainable routinely.

Particularly preferably, at least one oxidizing agent or reducing agent is added to the glass powder which is thermally activatable, i.e. develops its oxidative or reductive effect upon a change in temperature, in particular an increase in temperature. This is particularly advantageous when the subsequent change in the redox state of a glass component is associated with external thermal influences. The oxidizing agent or reducing agent is preferably chosen here such that it develops its effect in the temperature range in which the glass powder is subjected to external influences.

It is further advantageous for the oxidizing agent or reducing agent to be nontoxic. As well as general ecological requirements on a glass powder, this is particularly necessary in the case of use in the medical and dental sector.

The oxidizing agent or reducing agent can, however, generally be metered in such that no excesses of oxidizing agent or reducing agent are present in the glass powder when the reaction is complete.

The glass powder according to the invention is preferably used as dental glass powder, for example in a dental glass/plastic composite for tooth filling. Dental uses are disclosed in, e.g., DE 199 49 385 Al; DE 44 43 173 Al; U.S. Pat. No. 5,641,347 and DE 43 23 143 C1.

The entire disclosure of all applications, patents and publications, cited above or below, and of corresponding German application No. 199 35 707.2, filed Jul. 29, 1999, is hereby incorporated by reference.

EXAMPLES

In order to avoid the color change (darkening) caused during thermal post-treatment of a dental glass powder, a strong oxidizing agent, preferably about 0.5% by weight of $NH_4ClO_4$, was added to the glass powder. The original color change could be attributed to very small traces of titanium dioxide in the glass powder. In the temperature range of the thermal post-treatment of the glass powder, the titanium irreversibly changes its redox state and forms highly colouring mixed oxides. By adding $NH_4ClO_4$, it was possible to completely suppress this undesired color change. $NH_4ClO_4$, develops its oxidative action in the same temperature range in which the thermal post-treatment of the dental glass powder is carried out.

A further advantage of the $NH_4ClO_4$ addition is that the reaction or decomposition products following the thermal post-processing are nontoxic, $NH_4ClO_4$ can be added directly to the glass powder either as a solid powder or in the form of a solution.

In the case of the use of solid $NH_4ClO_4$, it has proven advantageous to add the $NH_4ClO_4$ to the glass powder during grinding in order to achieve a homogeneous distribution, However, any other mixing method which ensures homogeneous distribution is also conceivable.

The wet process is more simple in this connection. Here, in one wet-processing step, commercially available $NH_4ClO_4$ solution is added prior to the heat treatment. It is to be ensured here that homogenization in the wet state is ensured. Drying is later carried out as usual. Experiments showed that all drying procedures used for production did not impair the oxidation effect. A further advantage of the wet process is that there are no storage limitations for $NH_4ClO_4$ solution, in contrast to solid $NH_4ClO_4$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A glass powder comprising at least one oxidizing agent, which is $NH_4ClO_4$.

2. The glass powder according to claim 1, comprising an oxidizing agent in solid, liquid or gaseous form.

3. The glass powder according to claim 1, comprising an oxidizing agent which is thermally activatable.

4. The glass powder according to claim 1, comprising an oxidizing agent which is non-toxic.

5. The glass powder according to claim 1, wherein 0.01 to 1% by weight of $NH_4ClO_4$ is contained in the glass powder.

6. The glass powder according to claim 1, wherein 0.5 to 1% by weight of $NH_4ClO_4$ is contained in the glass powder.

7. The glass powder according to claim 1, wherein 0.01 to 1% by weight of oxidizing agent is contained in the glass powder.

8. The glass powder according to claim 1, wherein 0.5 to 1% by weight of oxidizing agent is contained in the glass powder.

9. The glass powder according to claim 1, wherein $NH_4ClO_4$ is in liquid form.

10. A glass powder according to claim 1, wherein 0.5% by weight of $NH_4ClO_4$ is contained in the glass powder.

11. A glass powder according to claim 1, wherein 0.5% by weight of oxidizing agent is contained in the glass powder.

12. A method for controlling the oxidation state of polyvalent cations in a glass, comprising adding an amount of an oxidizing agent to a glass powder prior to melting, wherein the oxidizing agent is $NH_4ClO_4$.

13. In a dental glass powder comprising a heat-meltable glass powder, the improvement wherein the heat-meltable glass powder is one according to claim 1.

14. A dental glass powder comprising a glass powder according to claim 1.

15. A dental glass plastic composite comprising a glass powder according to claim 1.

* * * * *